(12) United States Patent
Dobashi et al.

(10) Patent No.: US 11,033,278 B2
(45) Date of Patent: Jun. 15, 2021

(54) SYSTEMS AND METHODS FOR ENDOSCOPIC SUBMUCOSAL DISSECTION USING MAGNETICALLY ATTACHABLE CLIPS

(71) Applicant: Mayo Foundation for Medical Education and Research, Rochester, MN (US)

(72) Inventors: Akira Dobashi, Kashiwa (JP); Elizabeth Rajan, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 112 days.

(21) Appl. No.: 16/184,750

(22) Filed: Nov. 8, 2018

(65) Prior Publication Data

US 2019/0133591 A1    May 9, 2019

Related U.S. Application Data (60) Provisional application No. 62/583,079, filed on Nov. 8, 2017, provisional application No. 62/628,024, filed on Feb. 8, 2018.

(51) Int. Cl.
   *A61B 17/122*    (2006.01)
   *A61B 17/06*    (2006.01)
   (Continued)

(52) U.S. Cl.
   CPC ........ *A61B 17/122* (2013.01); *A61B 17/0218* (2013.01); *A61B 17/06166* (2013.01); *A61B 17/00234* (2013.01); *A61B 2017/00269* (2013.01); *A61B 2017/00477* (2013.01); *A61B 2017/00818* (2013.01); *A61B 2017/00876* (2013.01); *A61B 2017/0225* (2013.01); *A61B 2017/0464* (2013.01);
   (Continued)

(58) Field of Classification Search
   CPC ........... A61B 2017/00269; A61B 2017/00818; A61B 2017/00876; A61B 2017/1132–1139; A61B 17/122–1227; A61B 17/1114–2017/1117; A61F 5/0036; A61F 5/0013; A61F 2005/0016
   See application file for complete search history.

(56) References Cited

U.S. PATENT DOCUMENTS

| | | |
|---|---|---|
| 5,242,456 A | 9/1993 | Nash et al. |
| 5,415,666 A | 5/1995 | Gourlay et al. |

(Continued)

FOREIGN PATENT DOCUMENTS

| | | |
|---|---|---|
| EP | 1598020 A1 | 11/2005 |
| EP | 2578167 A1 | 4/2013 |

(Continued)

OTHER PUBLICATIONS

English machine translation of JP2008142516A, obtained from Espacenet on Jul. 10, 2020 (Year: 2008).*

(Continued)

*Primary Examiner* — Darwin P Erezo
*Assistant Examiner* — Brigid K Byrd (57) ABSTRACT

A method of performing an endoscopic submucosal resection includes using two magnet-attached hemostatic clips that are selectively coupled to one another via their respective magnets.

9 Claims, 13 Drawing Sheets

(51) Int. Cl.
*A61B 17/02* (2006.01)
*A61B 17/00* (2006.01)
*A61B 17/12* (2006.01)
*A61B 17/04* (2006.01)
*A61B 17/08* (2006.01)

(52) U.S. Cl.
CPC .............. *A61B 2017/06176* (2013.01); *A61B 2017/081* (2013.01); *A61B 2017/12004* (2013.01)

(56) References Cited

U.S. PATENT DOCUMENTS

| | | | |
|---|---|---|---|
| 5,509,923 | A | 4/1996 | Middleman et al. |
| 5,512,037 | A | 4/1996 | Russell et al. |
| 7,766,810 | B2 | 8/2010 | Ohdaira |
| 8,038,612 | B2 | 10/2011 | Paz |
| 8,136,888 | B2 | 3/2012 | Suzuki et al. |
| 8,137,268 | B2 | 3/2012 | Van Lue |
| 8,147,515 | B2 | 4/2012 | Ohdaira |
| 8,187,315 | B1 | 5/2012 | Clauson et al. |
| 8,360,972 | B2 | 1/2013 | Paz |
| 9,078,687 | B2 | 7/2015 | Rohaninejad et al. |
| 9,247,932 | B2 | 2/2016 | Lee |
| 9,265,525 | B2 | 2/2016 | Weitzner et al. |
| 9,463,003 | B2 | 10/2016 | Gordin et al. |
| 9,554,818 | B2 | 1/2017 | Rohaninejad et al. |
| 9,855,068 | B2 | 1/2018 | Rohaninejad et al. |
| 10,143,459 | B2 | 12/2018 | Heftman |
| 10,231,718 | B2 | 3/2019 | Ciulla et al. |
| 10,342,540 | B2 | 7/2019 | Smith et al. |
| 10,398,437 | B2 | 9/2019 | Machold et al. |
| 10,492,812 | B2 | 12/2019 | Rohaninejad et al. |
| 10,537,316 | B2 | 1/2020 | Smith et al. |
| 2004/0050395 | A1* | 3/2004 | Ueda ...................... A61B 90/00 128/899 |
| 2007/0093861 | A1* | 4/2007 | Vardi .................. A61B 17/1114 606/153 |
| 2008/0221599 | A1 | 9/2008 | Starksen |
| 2012/0289776 | A1 | 11/2012 | Keast et al. |
| 2015/0051642 | A1 | 2/2015 | Broom et al. |
| 2017/0035407 | A1 | 2/2017 | Duan et al. |
| 2017/0209132 | A1 | 7/2017 | Bhatt et al. |
| 2017/0258301 | A1* | 9/2017 | Lee ...................... A61B 17/083 |

FOREIGN PATENT DOCUMENTS

| | | |
|---|---|---|
| JP | 2004321482 A | 11/2004 |
| JP | 2005103107 A | 4/2005 |
| JP | 2008142516 A | 6/2008 |
| JP | 2008155006 A | 7/2008 |
| JP | 4320207 B2 | 8/2009 |
| JP | 4349847 B2 | 10/2009 |
| JP | 4373715 B2 | 11/2009 |
| JP | 4472680 B2 | 6/2010 |
| JP | 4514183 B2 | 7/2010 |
| KR | 101838553 B1 | 3/2018 |
| WO | 2009034922 A1 | 3/2009 |
| WO | 2010041714 A1 | 4/2010 |
| WO | 2012054845 A2 | 4/2012 |
| WO | 2014055193 A1 | 4/2014 |
| WO | 2018227592 A1 | 12/2018 |

OTHER PUBLICATIONS

International Search Report corresponding to the International Application No. PCT/US2017/014038, dated Apr. 5, 2017; 5 pages.
Australian Examination Report issued in corresponding Australian Application No. 2017209092, dated Nov. 30, 2018; 5 pages.
International Search Report and Written Opinion of the International Searching Authority, dated Feb. 20, 2019, corresponding to counterpart International Application No. PCT/US2018/059867; 15 total pages.
American Society for Gastrointestinal Endoscopy, vol. 2, No. 4, pp. 74-75, copyright 2017.

* cited by examiner

SYSTEMS AND METHODS FOR ENDOSCOPIC SUBMUCOSAL DISSECTION USING MAGNETICALLY ATTACHABLE CLIPS

CROSS-REFERENCE TO RELATED APPLICATIONS

This application claims the benefit of and priority to U.S. Provisional Patent Application No. 62/583,079, filed on Nov. 8, 2017, and U.S. Provisional Patent Application No. 62/628,024, filed on Feb. 8, 2018, the entire contents of each of which are incorporated by reference herein.

BACKGROUND

Endoscopic resection has been already accepted as a first choice of the treatment for early stage GI carcinomas because of less invasiveness and lower cost. Endoscopic submucosal resection (ESD) allows for an en bloc resection and accurate histopathological diagnosis regardless of the size, an existence of severe fibrosis at submucosal layer and location of a lesion. One of the benefits of ESD is lower recurrence rates compared to endoscopic mucosal resection.

SUMMARY

Magnetic anchor-guided endoscopic submucosal dissection (MAG-ESD) may deliver appropriate countertraction independent from an endoscopic longitudinal direction. Original MAG-ESD uses an extracorporeal electromagnetic control apparatus, which is large and cumbersome. The limitations of MAG-ESD are that a thicker abdominal wall causes a weaker attraction and the lesion is always attracted forward from the back side of a body because an external magnet cannot be placed at the back but at the front of the stomach.

Accordingly, effective countertraction is needed for safer and quicker endoscopic submucosal dissection (ESD). The disclosure provides magnet attached hemoclips (MAHs) for ESDs.

In accordance with an aspect of the disclosure, a suture for use with a hemostatic clip is provided and includes a plurality of looped segments coupled to one another, a magnet, and a stopper. Each of the looped segments is configured to be selectively coupled to a hemostatic clip. The magnet is attached to an end of one of the looped segments, and the stopper is slidable relative to the looped segments.

In accordance with another aspect of the disclosure, a method of performing an endoscopic submucosal resection is provided and includes deploying a first magnet-attached hemostatic clip adjacent a lesion; deploying a second magnet-attached hemostatic clip adjacent a gastric wall; and connecting respective magnets of the first and second clips.

BRIEF DESCRIPTION OF THE DRAWINGS

The accompanying drawings, which are incorporated in and constitute a part of the specification, illustrate embodiments of the disclosure and, together with a general description of the disclosure given above as well as the detailed description of the embodiment or embodiments given below, serve to explain the principles of this disclosure.

DETAILED DESCRIPTION

Figure 1:
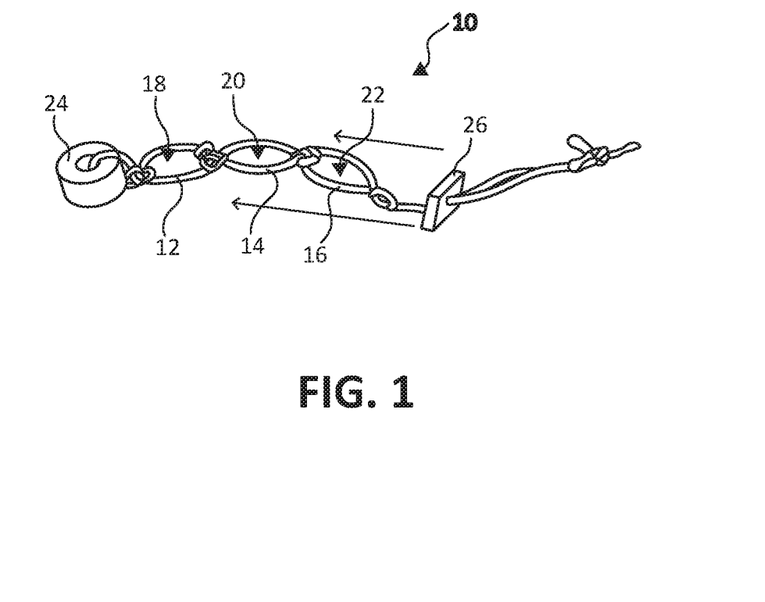
FIG. 1 is a side, perspective view of an example multi-stage suture for length adjustability of a magnetic traction device.
Figure 2:
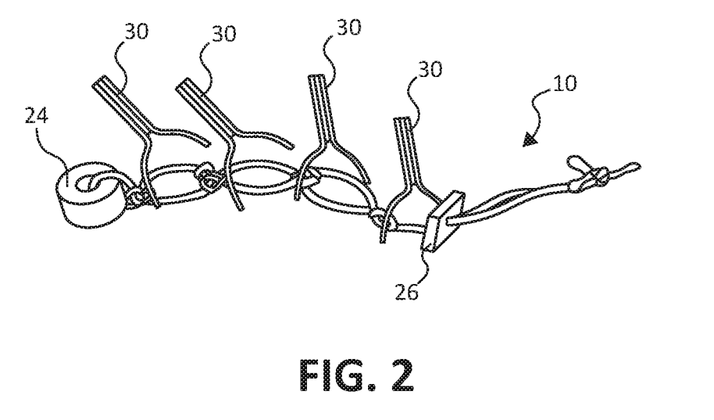
FIG. 2 is a side, perspective view of the suture of FIG. 1 with one or more hemoclips (MAHs) being attached thereto.

FIGS. 1 and 2 illustrate an exemplary embodiment of a multi-stage suture 10 for length adjustability of a magnetic traction device ("MTD"). The suture 10 has a plurality of looped segments 12, 14, 16 attached to one another. The looped segments 12, 14, 16 each define a hole 18, 20, 22 therethrough. A magnet 24 is attached to an end 10a of the suture 10 and a stopper 26 disposed at an opposite end 10b of the suture 10. The stopper 26 may be slidably disposed on the suture 10, such that the stopper 26 may adjust its axial position on the suture 10 during use. A hemoclip 30 may be selectively secured to any of a variety of locations of the suture 10, for example, to one of the looped segments 12, 14, 16. In some aspects, a jaw of each of the hemoclips 30 may be received in a respective hole 18, 20, 22 of the looped segments 12, 14, 16, whereby the looped segments 12, 14, 16 may be secured about the jaw to fix the hemoclips 30 to the suture 10. The hemoclips 30 may be secured by the stopper 26 to achieve a favorable suture length for the magnetic traction device. Upon receiving a jaw or jaws of the hemoclip 30 in the hole 18, 20, or 22 of the suture 10, the stopper 26 secures the hemoclip 30 in place.

Figure 3:
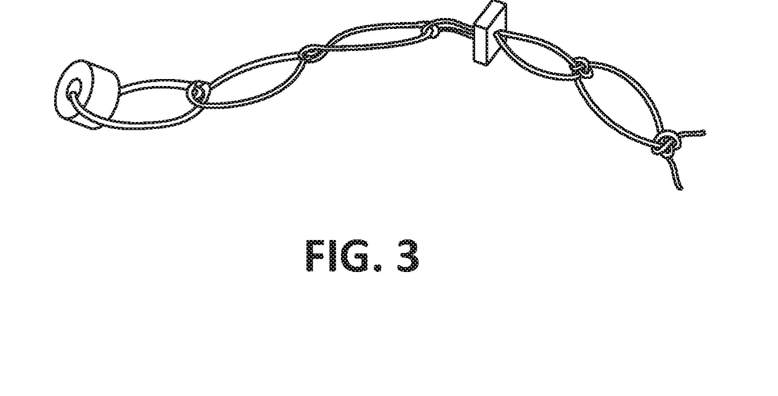
FIG. 3 is a side, perspective view of a nylon-fabricated multi-stage suture for length adjustability of a magnetic traction device.
Figure 4:
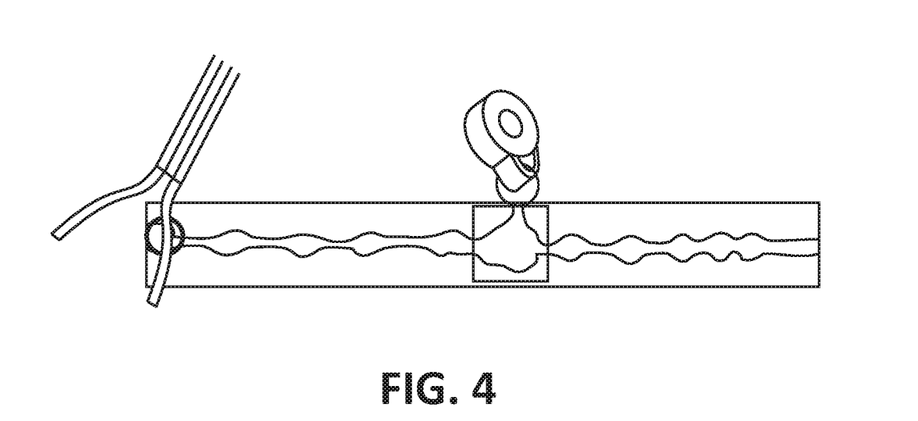
FIG. 4 shows an example magnetic traction device with length adjustability through a zip-tie like structure.
Figure 5:
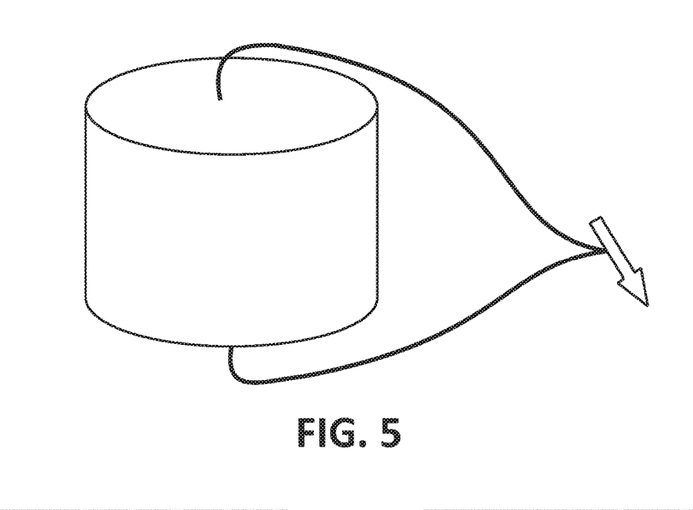
FIG. 5 is a side, perspective view of an example magnetic closure device, with a T-tag or a clip attached to a magnet.
Figure 6A:
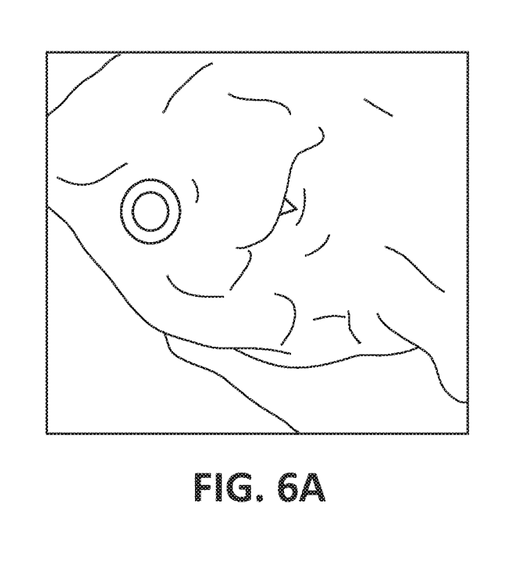
FIGS. 6A and 6B show an example deployment of a magnetic closure device.
Figure 6B:
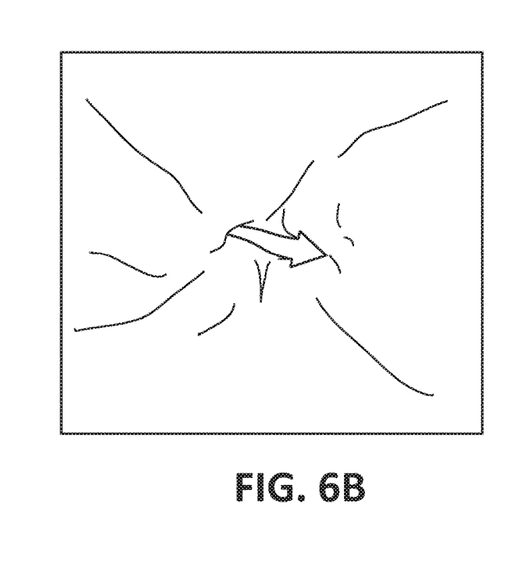
Figure 7A:
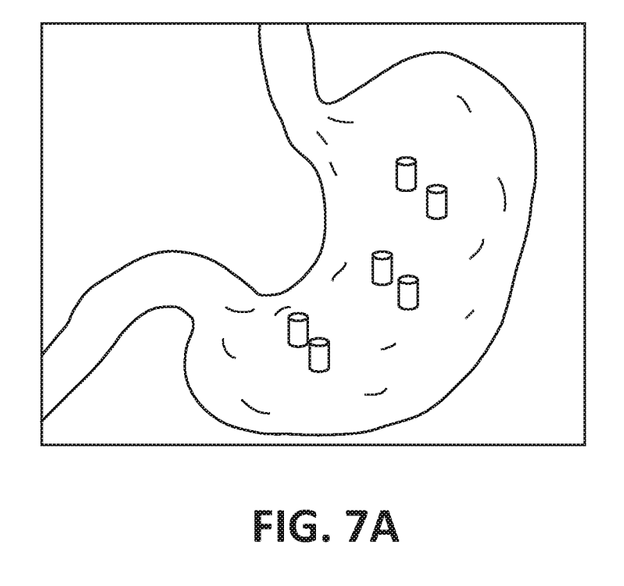
FIGS. 7A and 7B show an example deployment of three pairs of magnetic closure devices.
Figure 7B:
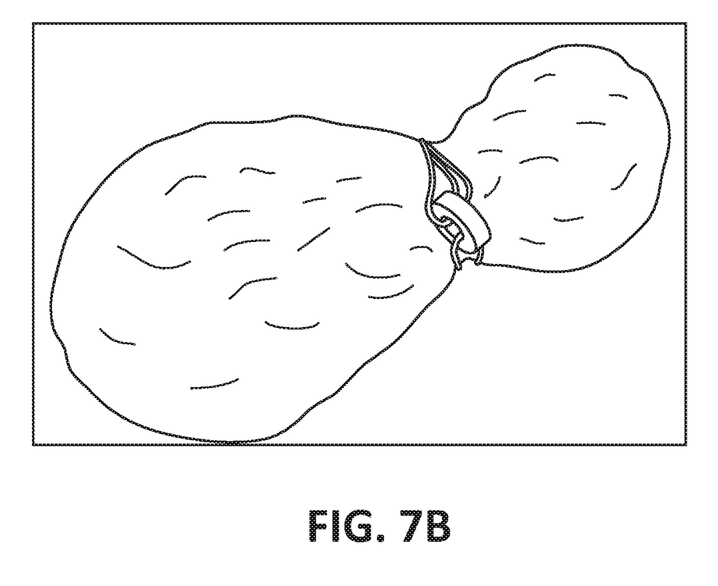
Figure 8:
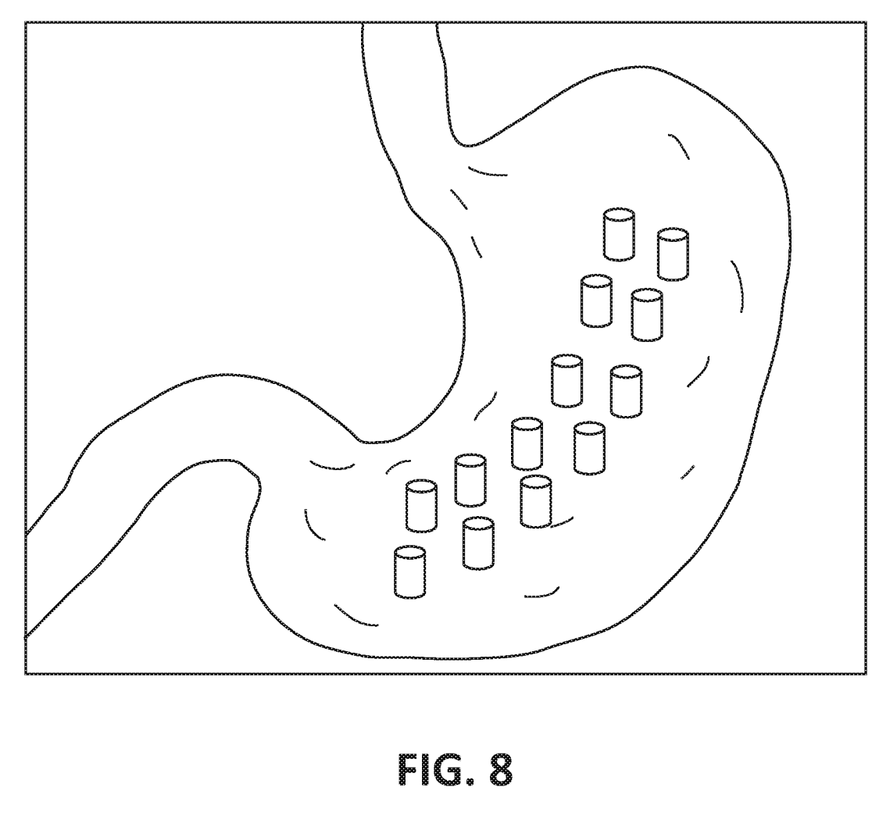
FIG. 8 shows another example deployment of magnetic closure devices.
Figure 9A:
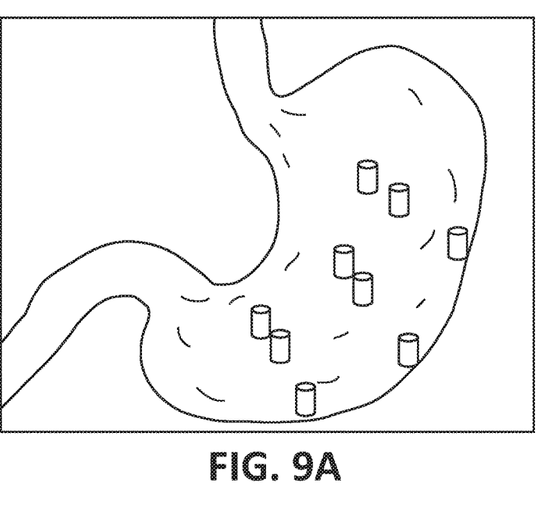
FIGS. 9A-9C show another example deployment of magnetic closure devices.
Figure 9B:
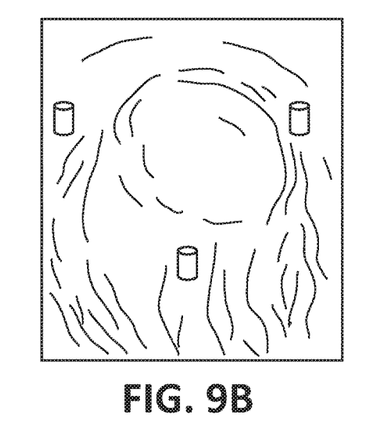
Figure 9C:
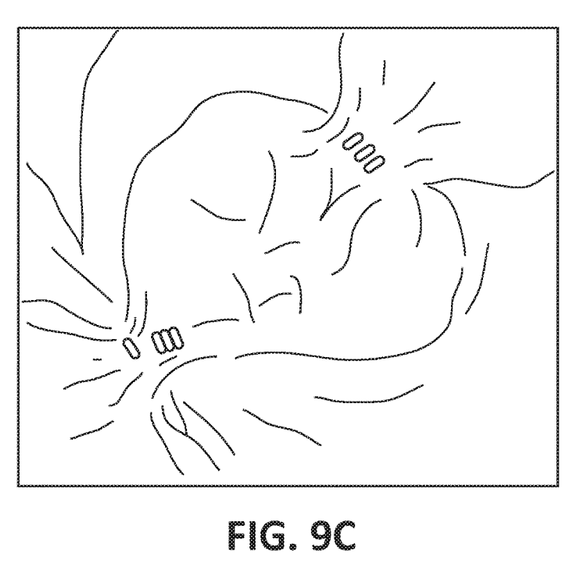
Figure 10A:
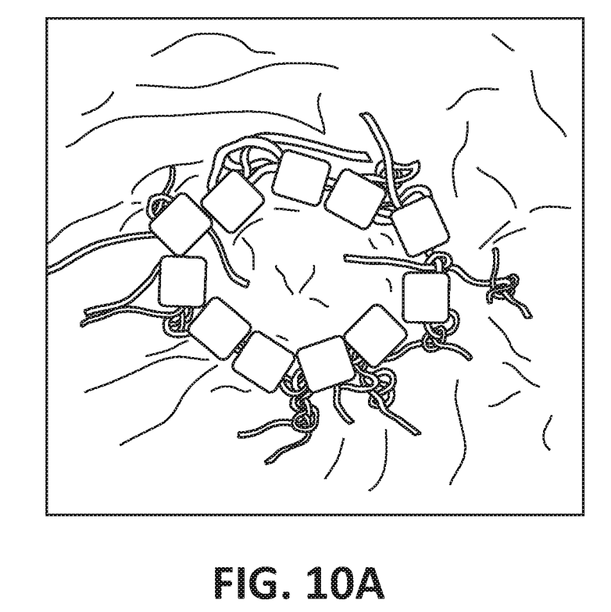
FIGS. 10A and 10B show another example deployment of magnetic closure devices.
Figure 10B:
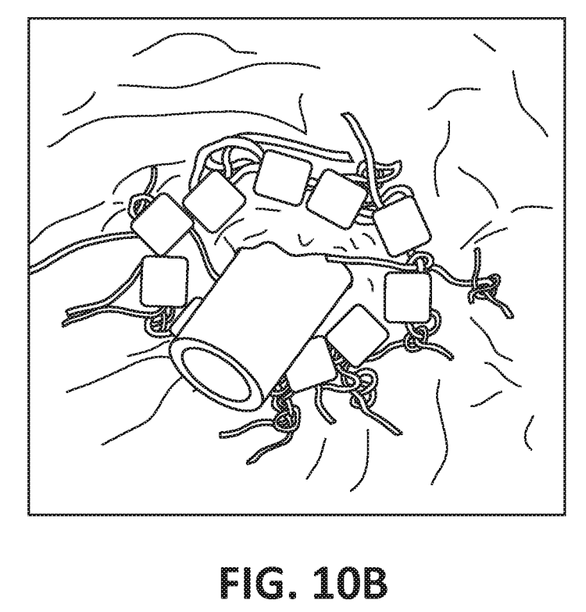

In aspects, with reference to FIG. 3, the multi-stage suture for MTD may be fabricated from nylon or any other suitable material. FIG. 4 shows an example of a MTD with length adjustability through a zip tie like structure. FIG. 5 shows an example of a Magnet Closure Device (MCD). In this embodiment (as shown) a T-tag is attached to a magnet. Alternatively, a clip can be attached to the magnet (not shown in FIG. 5). FIGS. 6A and 6B show an example of MCD deployed in a full-thickness manner. The T-tag was deployed by piercing through stomach wall then reentered and embedded within stomach wall for anchoring. The magnet is retained on the mucosal side, while sutures can be seen from the serosal side. FIGS. 7A and 7B show an example of 3 pairs of MCDs deployed at anterior surface and posterior surface of stomach, attraction between MCDs deployed at anterior surface and MCDs at posterior surface of stomach reduce gastric volume to treat obesity. FIG. 8 shows an example of MCDs deployed linearly on anterior surface and posterior surface of stomach. FIGS. 9A-9C show an example of three pairs of MCDs deployed at an anterior surface, posterior surface and greater curvature of stomach and/or lesser curvature of stomach. Attraction between MCDs reduce gastric volume. FIGS. 10A and 10B show an example of MCDs deployed at cardia in a circular pattern for Gastroesophageal Reflux Disease (GERO).

Figure 11A:
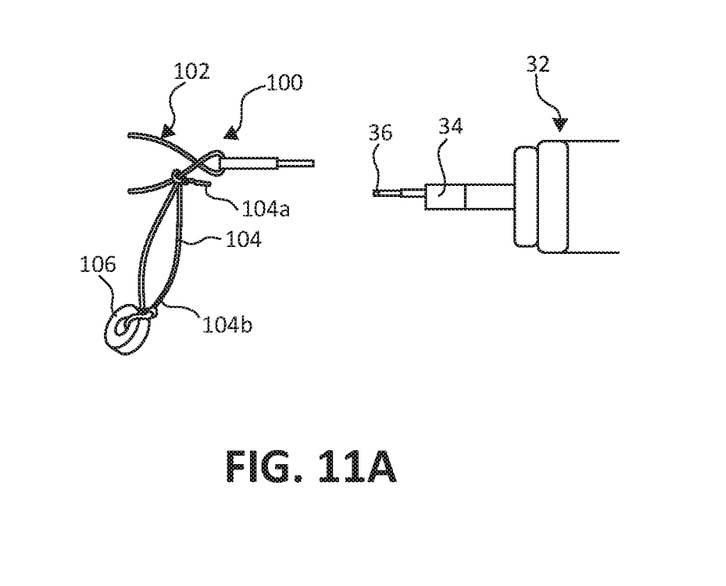
FIG. 11A is a side view of a magnet-attached hemoclip detached from an endoscope.

With reference to FIGS. 11A-18, a method for performing a submucosal dissection is provided that includes utilizing two or more magnet-attached hemoclips ("MAH") 100, 200. With reference to FIGS. 11A and 11B, an endoscope 32 has a retractable shaft 34 extending therefrom having a distal tip 36 configured for detachable engagement with the MAH 100 or 200. The MAH 100 has a pair of jaws 102 configured to move between open and closed configurations, a suture 104 having a first end 104a secured to one of the jaws 102, and a magnet 106 attached to a second end 104b of the suture 104. Each of the MAHs 100, 200 have the same or substantially similar features. Accordingly, details of MAH 200 will not be further described.

In operation, a circumferential mucosal incision 110 (FIG. 12B) is completed by a needle knife along the markings 112 (FIG. 12A), which may be made with a 30 mm paper round template. The first MAH 100 is deployed at the edge of the lesion 114 and the second MAH 200 is deployed at the other side of gastric wall after magnets 106, 206 connect to each other in a stomach. Submucosal dissection may be performed using a needle knife. After a removal of the lesion 114, MAHs 100, 200 and the target lesion 114 are retrieved by a snare.

In total, 10 ESDs were performed with MAHs (ESD-MAHs) and without MAHs (conventional ESD), respectively. En bloc resection was successfully completed without perforation in all cases. The submucosal dissection time in ESD-MAHs was significantly shorter than that in conventional ESD (median: 385 seconds [interquartile range: 273-254] vs.865 seconds [interquartile range: 709-1080], $p<0.05$). The visualization score of submucosal layer during dissection in ESD-MAHs was significantly higher than that in conventional ESD (median: 5 [interquartile range: 4-5] vs.3 [interquartile range: 2-4], $p<0.05$) and the number of muscular injuries was significantly smaller in ESD-MAHs than that in conventional ESD (median: 0 [interquartile range: 0-0] vs.1 [interquartile range: 0-2], $p<0.05$).

MAHs provide excellent countertraction and enable safer and faster gastric ESD.

EXAMPLE

The Example that follows is set forth to aid in understanding the invention but is not intended to, and should not be construed to, limit its scope in any way.

Materials and Methods

Prepararion of a Stomach

Five whole swine stomachs with esophagus from pigs of similar size (50-60 kg) were used. The stomachs were inverted from the incision at the greater curvature in the upper body and cautery markings were made by argon plasma coagulation (Genii, St Paul, Minn.) along a 30 mm paper round template on five different areas as previously reported; the anterior and posterior wall in the lower gastric body, the greater curvature in the middle gastric body, and the anterior and posterior wall in the upper gastric body. Stomachs were everted followed by closing the incisions by suturing and then those were contained and fixed by rubber bands in a commercial ex vivo trainer (Endo-X-Trainer, Medical Innovations, Rochester, Minn.). An overtube (00711147; US endoscopy, Mentor, Ohio) was inserted through the esophagus.

Magnet Attached Hemoclip (MAH)

Figure 11B:
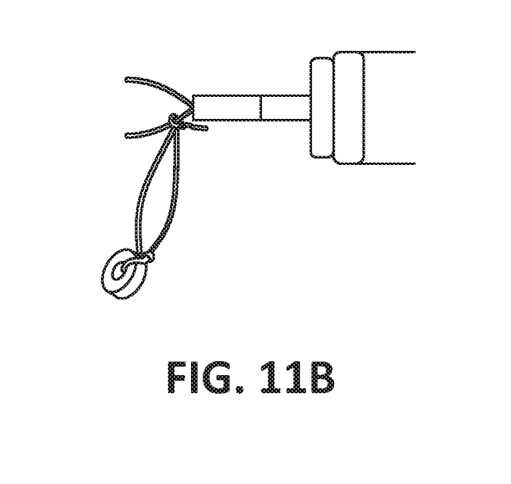
FIG. 11B is a side view of the magnet-attached hemoclip of FIG. 11A attached to the endoscope.
Figure 12A:
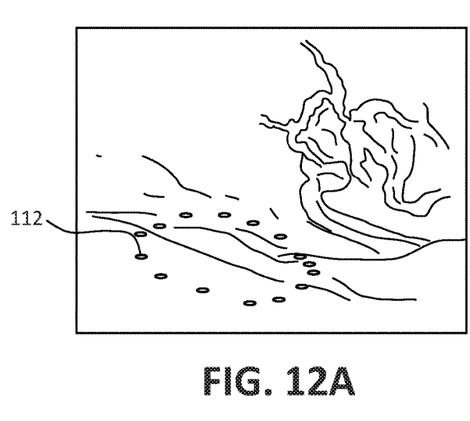
FIG. 12A shows a lesion located at a posterior gastric wall in the upper body.
Figure 12B:
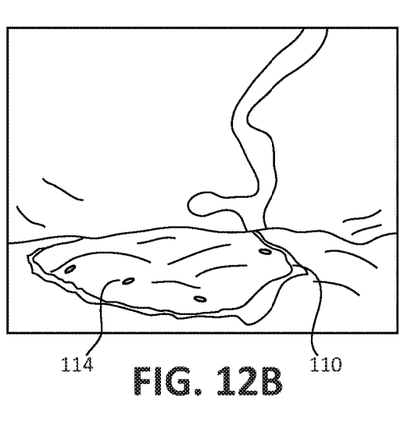
FIG. 12B shows a completed circumferential incision in the posterior gastric wall.
Figure 12C:
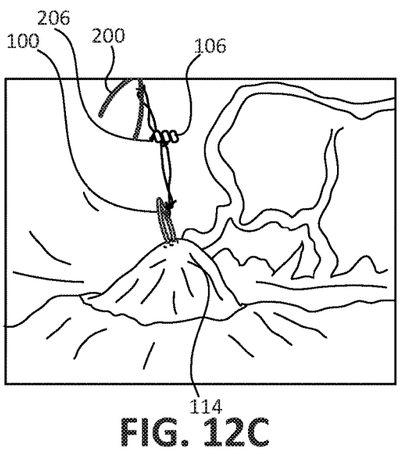
FIG. 12C shows two MAHs deployed and connecting the lesion at the posterior gastric wall and the other side (anterior) of the gastric wall.
Figure 12D:
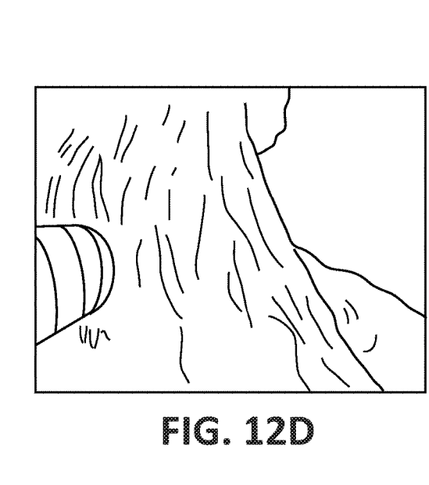
FIG. 12D shows a clear visualization during submucosal dissection by MAHs countertraction.
Figure 12E:
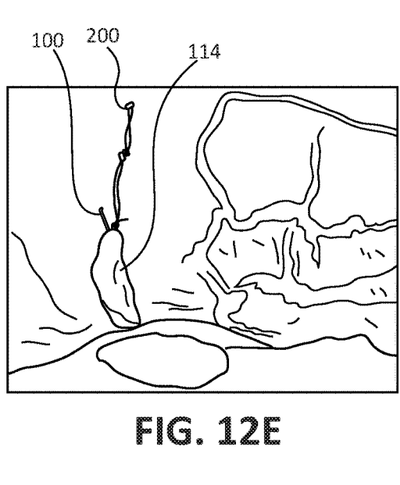
FIG. 12E illustrates the lesion being removed without muscular injuries.
Figure 12F:
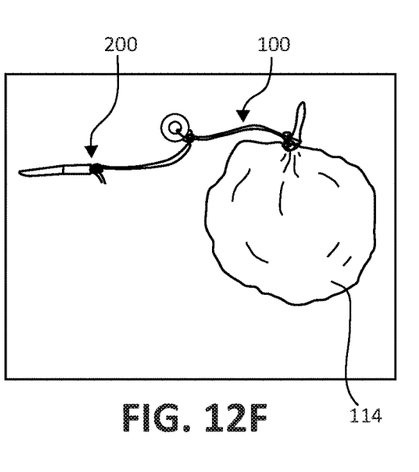
FIG. 12F shows a resected lesion with the two MAHs attached via their respective magnets.
Figure 13A:
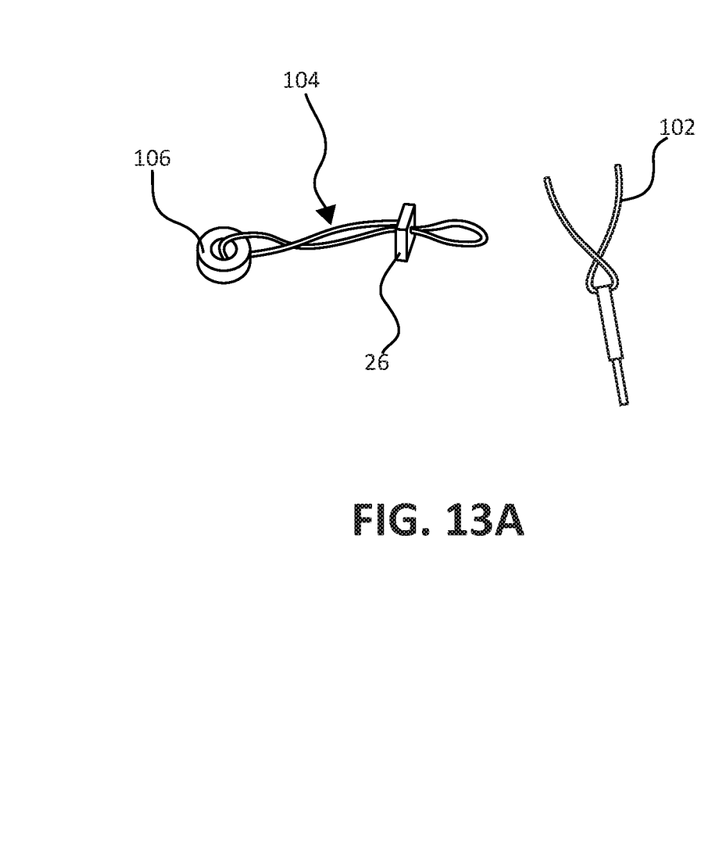
FIG. 13A is an exploded view of a the magnet-attached thermoclip.
Figure 13B:
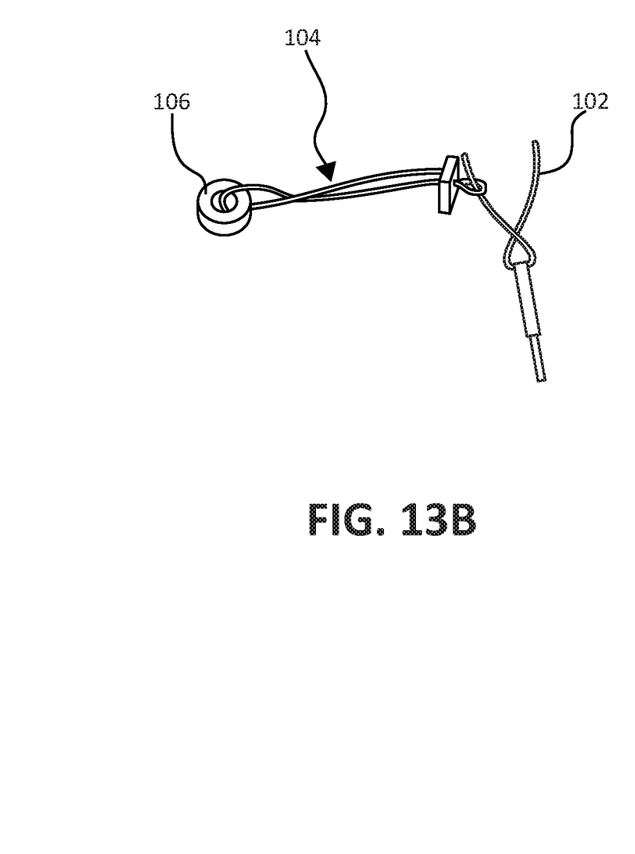
FIG. 13B is a perspective view of the MAH of FIG. 13A in an assembled state.
Figure 14:
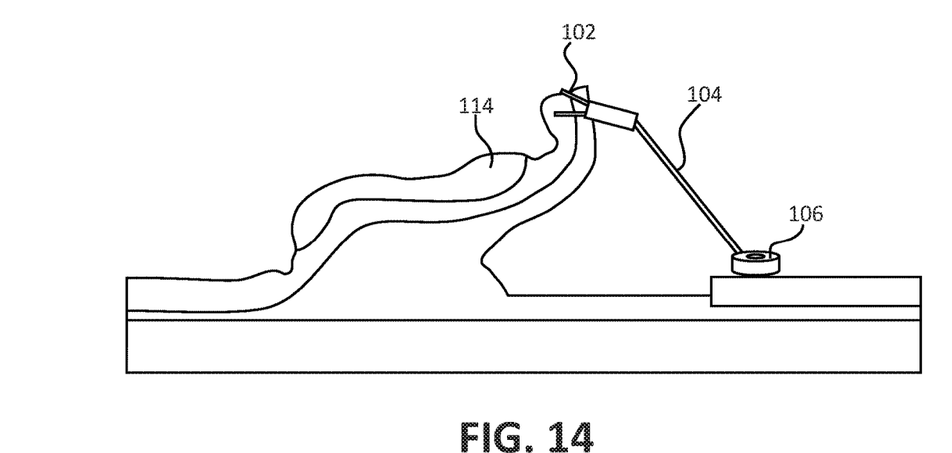
FIG. 14 is a side view of the MAH of FIG. 13A secured to the lesion.
Figure 15:
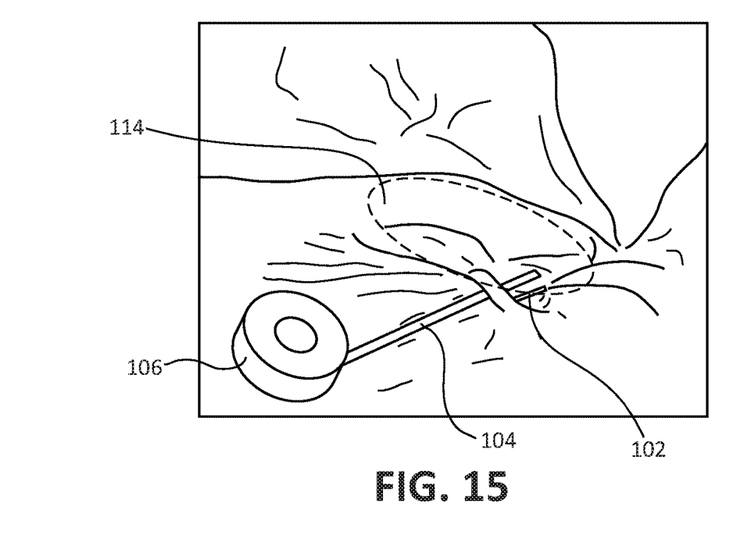
FIG. 15 is a perspective view of the MAH of FIG. 13A secured to the lesion.
Figures 16, 17:
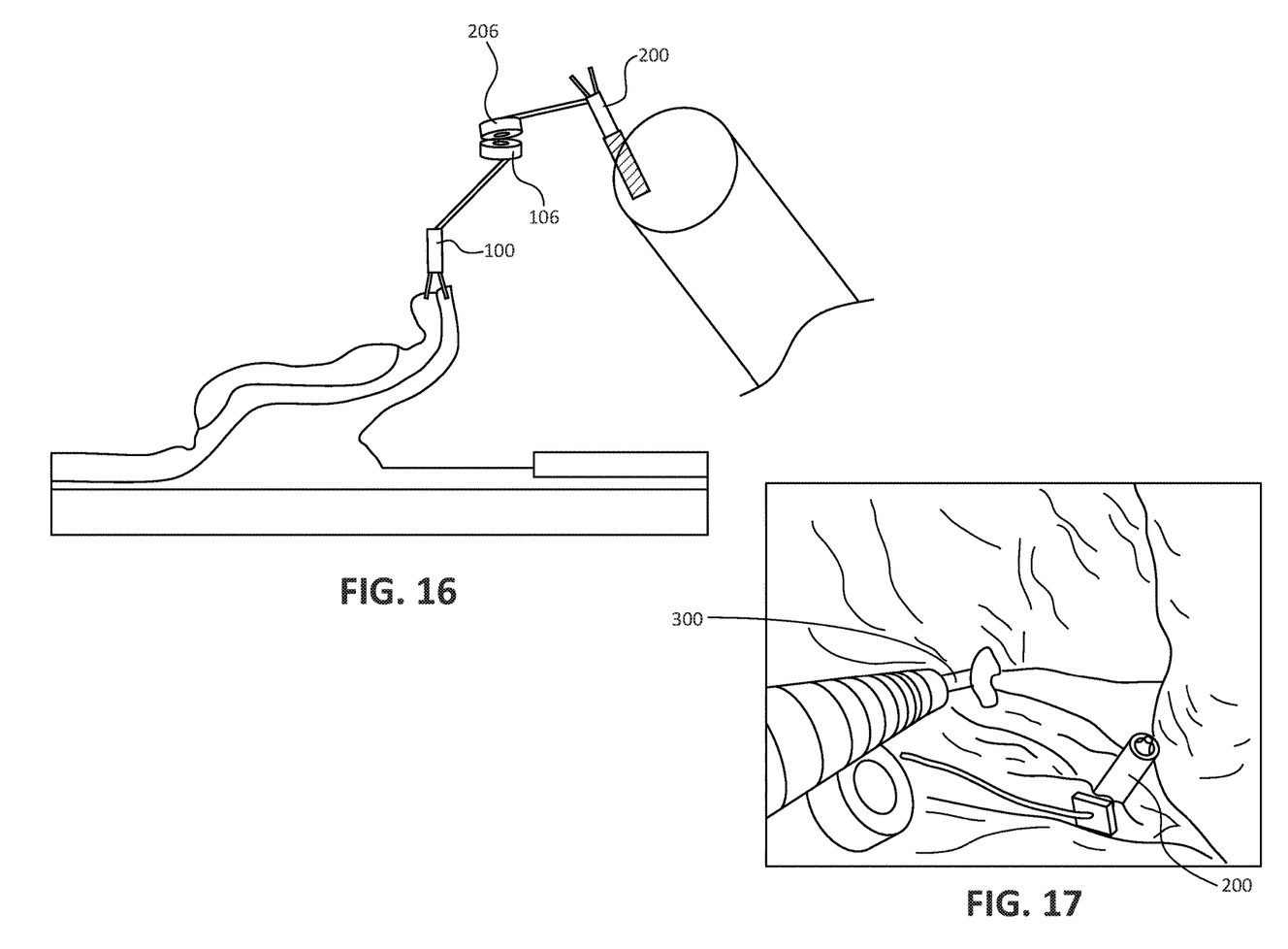
FIG. 16 illustrates the pair of MAHs secured to one another by their respective magnets.
FIG. 17 is a top view of the pair of MAHs coupled between an endoscopic tool and the lesion.
Figure 18:
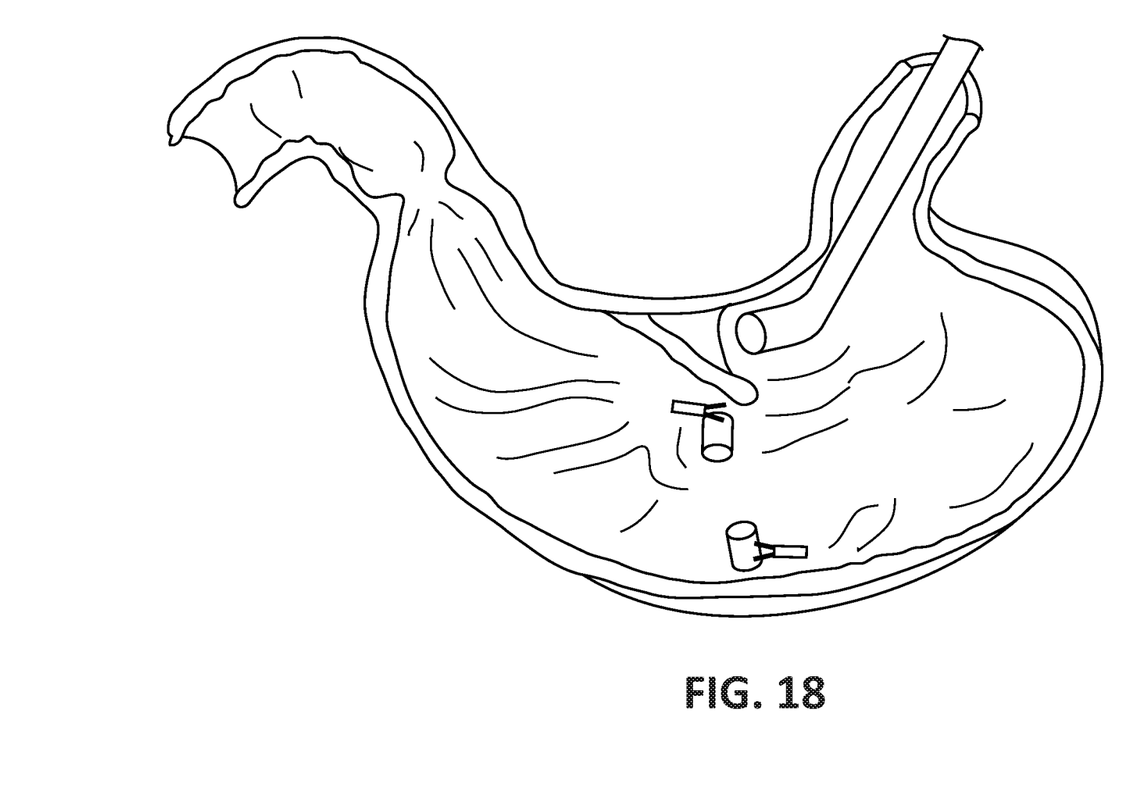
FIG. 18 is a side cross-sectional view of a stomach illustrating a pair of MAHs utilized in carrying out an endoscopic submucosal resection.

A Neodymium ring magnet (R212: $1/8$" od X $1/16$" id X $1/8$" thick, N42, 0.53 lb or R311: $3/16$" od X $1/16$" id X $1/16$" thick, N42, 0.7 lb) was attached to a hemoclip with a 2-0 silk suture. The length of the suture between a hemoclip and a magnet was 2 cm. When the hemoclip, which can be separated from a hemoclip applicator device, was used, a magnet was attached to a hemoclip in advance (FIG. 11A) and the MAH was mounted after passage down the endoscopic working channel of a hemoclip applicator device. In some aspects, the magnet may be tied with a hemoclip during ESD procedure after the clip went through the endoscopic working channel (FIG. 11B).

ESD Procedure with MAHs

A standard gastroscope with a transparent hood was used and all procedures were performed by an endoscopist (A.D.), an expert in ESD including more than 400 cases. At first, a circumferential mucosal incision (40 W pulse coagulation; Genii) was completed by a needle knife along the markings after the injection of saline solution with indigo carmine dye into the submucosal layer. Then, the endoscope was withdrawn and reinserted with a MAH. The first MAH was deployed at the edge of the lesion and then the second MAH was deployed at the other side of the gastric wall after the respective magnets connected each other in the stomach. Submucosal dissection was performed using an electrosurgical knife and the lesion was completely removed. After the resection, two MAHs and the lesion were retrieved by a crescent snare together.

Outcome Measurement

The primary outcome measure was the comparison of submucosal dissection time between conventional endoscopic submucosal dissection ("C-ESD") and ESD with MAHs (ESD-MAHs). The secondary outcome measures included rate of en bloc resection, the time of MAH deployment, the volume of injection into submucosal layer, total procedural time including the deployment of MAHs, specimen size, the visualization of submucosal layer during dissection, the number of muscular injuries, and the usability of MAHs. The visualization and usability were evaluated by using a visual analog scale ranging from 1 (poor) to 5 (excellent).

Statistical Analysis

The results were statistically analyzed based on the comparison of C-ESD and ESD-MAHs. Quantitative parameters were compared using Student's t test or the Mann-Whitney U test and qualitative parameters with Pearson's $\chi 2$ test. $P<0.05$ will be considered statistically significant. Statistical analysis was performed by using Stata 12.0 software (Stata Corp, College Station, Tex., USA).

Results

In total, 10 cases were performed in C-ESD and ESD-MAHs, respectively. Table 1 shows the results of each procedure. All lesions (20/20; 100%) both in C-ESD and ESD-MAHs were completed en bloc resection without perforation. Smaller magnets (R212) were used in initial two cases of ESD-MAHs. In the second case at posterior wall in the lower gastric body, MAHs disconnected each other and appropriate countertraction was not able to be obtained because of the tension of countertraction was stronger than the magnetic attraction. Thus, only MAH attached at the other side of gastric wall was retrieved by a snare and a MAH with a larger and stronger magnet (R311) was redeployed. Eventually, the magnets maintained connecting during the whole procedure with appropriate countertraction. After the second case, a larger magnet (R311) was used for all remaining cases. All MAHs were deployed and retrieved endoscopically.

The median time of MAH deployment was 205 seconds (interquartile range [IQR]: 163-211). The submucosal dissection time in ESD-MAHs was significantly shorter than that in C-ESD (median: 385 seconds [IQR: 273-254] vs.865 seconds [IQR: 709-1080], $p<0.05$). The volume of injection into submucosal layer in MAG-ESD for submucosal dissection was significantly smaller than that in C-ESD (median: 4 ml [IQR: 3-5] vs.12 ml [IQR: 6-13], $p<0.05$). There was no difference in total procedure time including MAH deployment in ESD-MAHs (median: 1261 seconds [IQR: 1211-1391] vs.1451 seconds [IQR: 1044-1932], $p=0.2889$). There was no difference in the specimen size. The visualization score of submucosal layer during dissection in ESD-MAHs was significantly higher than that in C-ESD (median: 5 [IQR: 4-5] vs.3 [IQR: 2-4], $p<0.05$) and the number of muscular injuries was significantly smaller in ESD-MAHs than that in C-ESD (median: 0 [IQR: 0-0] vs.1 [IQR: 0-2], $p<0.05$). The usability score of MAH was excellent (median: 5 [IQR: 5-5]).

Table 2 shows results of the subgroup analysis based on the lesion location (anterior wall vs. posterior wall and greater curvature). The visualization score of submucosal layer in C-ESD was significantly lower for lesions at posterior gastric wall (median: 2 [IQR: 1-2] vs. 5 [IQR: 4-5], $p<0.05$). There were significant differences between ESD-MAHs and C-ESD in total procedural time, submucosal dissection time, the number of muscular damage for lesions in posterior gastric wall and greater curvature. On the other hand, there was no difference in those parameters for lesions in anterior gastric wall.

TABLE 1

The results of procedures for endoscopic submucosal dissections with and without magnet attached hemoclips.

|  | ESD with MAHs (n = 10) | Control (n = 10) | P* value |
|---|---|---|---|
| Total procedure time (second); medium (IQR) | 1261 (1211-1391) | 1451 (1044-1932) | 0.289 |
| Circumferential incision (second); medium (IQR) | 613 (503-732) | 583 (413-790) | 0.940 |
| MAHs deployment (second); medium (IQR) | 205 (163-211) | — | — |
| Submucosal dissection (second); medium (IQR) | 385 (273-524) | 865 (709-1080) | <0.05 |
| Total volume of injection (ml); medium (IQR) | 25 (23-28) | 28 (20-31) | 0.382 |
| Injection during the circumferential incision (ml); medium (IQR) | 20 (16-21) | 17 (14-19) | 0.224 |
| Injection during submucosal dissection (ml); medium (IQR) | 4 (3-5) | 12 (6-13) | <0.05 |
| Specimen size (mm); medial (IQR) | 38 (36-40) | 39 (36-40) | 0.908 |
| Visualization score during submucosal dissection **; medium (IQR) | 5 (4-5) | 3 (2-4) | <0.05 |
| Number of muscular injuries; medium (IQR) | 0 (0-0) | 1 (0-2) | <0.05 |
| Usability score of MAH**; medium (IQR) | 5 (5-5) | — | — |

TABLE 2

The result of subgroup analysis based on the location of lesions.

|  | ESD with MAHs | control | P* value |
|---|---|---|---|
| Visualization score** during submucosal dissection; medium (IQR) |  |  |  |
| Anterior gastric wall | 5 (5-5) | 5 (4-5) | 0.127 |
| Posterior gastric wall and greater curvature | 5 (4-5) | 2 (1-2) | <0.05 |
| Total procedure time (second)***; medium (IQR) |  |  |  |
| Anterior gastric wall | 1130 (930-1232) | 1023 (786-1199) | 0.564 |
| Posterior gastric wall and greater curvature | 1379 (1265-1467) | 1751 (1490-1989) | <0.05 |
| Submucosal dissection time (second); medium (IQR) |  |  |  |
| Anterior gastric wall | 315 (249-375) | 673 (403-804) | 0.248 |
| Posterior gastric wall and greater curvature | 522 (375-716) | 1019 (845-1189) | <0.05 |
| Number of muscular injuries; medium (IQR) |  |  |  |
| Anterior gastric wall | 0 (0-0) | 0 (0-1) | 0.317 |
| Posterior gastric wall and greater curvature | 0 (0-1) | 2 (1-2) | <0.05 |

Discussion

This is the first report of MAG-ESD using dual MAHs. This ex vivo study investigated the effectiveness of MAHs for gastric ESD. En bloc resection was successfully completed and MAHs were retrieved in all cases immediately after the completion of the lesion. The results showed ESD-MAHs enable excellent visualization of submucosal layer, shorter time of submucosal dissection, and less injuries of muscular layer. The appropriate countertraction by MAHs could provide faster and safer ESD procedure.

MAG-ESD was originally reported with an extracorporeal electromagnetic control apparatus, which was used as an external magnet. Other reports about MAG-ESD also used both an external magnet and an internal magnet. The disadvantages of using an external magnet are thought that an extremely stronger external magnet is needed, the magnetic attraction is decreased by the thick abdominal wall because the distance between an internal magnet inside of the stomach and an external magnet outside of the body becomes far, and the direction of countertraction is limited within a three-dimensional hemisphere (i.e. external magnet can be put only in front of the body). To conquer those difficulties, we used dual MAHs as internal magnets.

Clear visualization of the dissection plane is necessary for safer and quicker ESD, but an endoluminal endoscope in itself can't allow an appropriate countertraction. That is because the therapeutic channel of an endoscope is occupied with an electrosurgical knife and ESD is performed by what is called "one-hand surgery method." To overcome the obstacle, several methods are reported to provide the appropriate traction during submucosal dissection such as clip-with-line method, percutaneous traction method, sinker-assisted method, external forceps method, internal-traction methods (clip band method, medical ring method, and S-O clip method), double-channel method, robot-assisted method. However, most of tractions except for internal-traction methods were done from distal to proximal side of GI tract through gastroesophageal junction (i.e. a parallel direction with the endoscopy) and the traction is not provided effectively in some cases.

An S-O clip was developed and has already used clinically as the countertraction device in a colon and a stomach. An S-O clip is composed of a hemoclip, a spring and a ling for another hemoclip. S-O clips are classified as an internal-traction method and the fundamental function is almost the same with MAHs method. The internal-traction method can determine the direction of the traction as favorable, which works extremely well for ESD. However, S-O clips have some limitation such as grasping the S-O clip by another hemoclip was occasionally prolonged and it took over 5 minutes to deploy in some cases. In addition, the spring of the S-O clip may be broken if the spring is stretched over 8 cm. One of the benefits of MAH is that two MAHs can be easily connected with magnetic force in a stomach. Another benefit is thought that MAHs can prevent an extensive traction, because an extensive tension causes disconnection of MAHs instead of causing the lesion injury. In other words, the magnets can work as a safety apparatus. The MAH system can also change the direction of countertraction easily after the deployment of MAHs because the MAH at the gastric wall side can be retrieved quickly by a snare and another MAH can be added such as secondary case of ESD-MAHs in this study.

Most lesions located at gastric anterior wall were able to obtain good visualization of submucosal layer without MAH (Table 2) because of the countertraction caused by gravity. However, the lesions at posterior gastric wall couldn't obtain appropriate counter traction without MAH and it was very difficult to recognize the submucosal layer during dissection. As a result, muscular layer was damaged by a needle knife and such lesions needed longer procedural time. All lesions may not be good candidates for MAHs because the deployment of MAHs needs a few minutes and in fact there was no difference in total procedural time and muscular injuries between C-ESD and ESD-MAHs. When MAHs are used for the lesions for which good visualization for submucosal layer can't be obtained, we can make the most effective use of MAHs.

In conclusion, we have developed MAG-ESD with dual MAHs. MAHs provided excellent countertraction. The improved visualization of submucosal layer enabled safer and faster gastric ESD in this study. If MAHs are used in a case without good visualization of submucosal layer, MAHs can become more effective device for countertraction.

ESD; endoscopic submucosal dissections, MAH; magnet attached hemoclip, *; Mann-Whitney U test, ; Scales were evaluated based on a visual analog scale (0=poor, 5=excellent),*; including deployment of magnet clips.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:
1. A method of performing an endoscopic submucosal dissection, comprising:
   deploying a first clip adjacent a lesion, the first clip including:
      a pair of jaws;

a tether having a first end coupled to the pair of jaws; and a magnet attached to a second end of the tether;

deploying a second clip adjacent a gastric wall, the second clip including:

a pair of jaws;

a tether having a first end coupled to the pair of jaws of the second clip; and a magnet attached to a second end of the tether of the second clip; and coupling the magnet of the first clip and the magnet of the second clip to one another.

2. The method according to claim 1, further comprising attaching the first clip to the lesion.

3. The method according to claim 2, wherein attaching the first clip to the lesion includes grasping a portion of the lesion with a first the pair of jaws of the first clip.

4. The method according to claim 3, further comprising grasping a portion of the gastric wall with the pair of jaws of the second clip.

5. The method according to claim 4, wherein the tethers of the first and second clips are tautened in response to coupling the magnets of the first and second clips to one another, such that the lesion is held in spaced relation from a muscle layer of the gastric wall.

6. The method according to claim 1, further comprising holding the lesion in spaced relation from a muscle layer of the gastric wall by the coupled first and second clips.

7. The method according to claim 6, further comprising dissecting the lesion from the muscle layer while the lesion is held in spaced relation from the muscle layer.

8. The method according to claim 6, further comprising:

making a circumferential mucosal incision around the lesion; and dissecting the lesion from the muscle layer.

9. The method according to claim 1, wherein the second clip is deployed adjacent the gastric wall after coupling the magnets of the first and second clips to one another.

* * * * *